US005480867A

United States Patent [19]

Merrifield et al.

[11] Patent Number: 5,480,867

[45] Date of Patent: Jan. 2, 1996

[54] GLUCAGON ANALOGS WITH SERINE REPLACEMENTS

[75] Inventors: Robert B. Merrifield, Creskill, N.J.; Cecilia G. Unson, New York, N.Y.

[73] Assignee: The Rockefeller University, New York, N.Y.

[21] Appl. No.: 255,558

[22] Filed: Jun. 8, 1994

Related U.S. Application Data

[63] Continuation of Ser. No. 175,137, Dec. 29, 1993, abandoned.

[51] Int. Cl.$^6$ .......................... A61K 38/26; C07K 14/00; C07K 14/605

[52] U.S. Cl. .............................................. 514/12; 530/308

[58] Field of Search ............................... 514/12; 530/308

[56] References Cited

U.S. PATENT DOCUMENTS 4,879,273 11/1989 Merrifield ................................ 514/12
5,143,902 9/1992 Merrifield et al. ........................ 514/12

FOREIGN PATENT DOCUMENTS

WO92/04042 3/1992 WIPO .
WO92/12998 8/1992 WIPO .

OTHER PUBLICATIONS

Unson et al., 1994, "Multiple–site replacement analogs of glucagon. A molecular basis for antagonists design", J. Biol. Chem 269:12548–51.

Unson and Merrifield, 1994, "Identification of an essential serine residue in glucagon: Implication for an active site triad", Proc. Natl. Acad. Sci USA 91:454–58.

Unson et al., 1993, "The role of histidine–1 in glucagon action", Arch. Biochem. Biophys. 300:747–50.

Unson et al., 1991, "Position 9 replacement analogs of glucagon uncouple biological activity and receptor binding", J. Biol. Chem. 266:2763–66.

Unson et al., 1989, "Glucagon antagonists: contribution to binding and activity of the amino–terminal sequence 1–5, position 12, and the putative alpha–helical segment 19–27", J. Biol. Chem. 264:789–94.

*Primary Examiner*—Jill Warden
*Assistant Examiner*—Benet Prickril
*Attorney, Agent, or Firm*—Klauber & Jackson

[57] ABSTRACT

Glucagon analogs characterized principally by the removal or replacement of the 9-aspartic acid residue or its replacement with another amino acid residue together with replacement of the 16-serine residue and possible replacement of the 11-serine residue and 21-aspartic acid residue with or without a histidine at the amino terminal are useful adjuncts to insulin therapy.

37 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

-continued ( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide
( A ) DESCRIPTION: glucagon ( i i i ) HYPOTHETICAL: No ( i v ) ANTI-SENSE: NO ( x i ) SEQUENCE DESCRIPTION: SEQ ID NO:1:

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

( 2 ) INFORMATION FOR SEQ ID NO:2:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide
( A ) DESCRIPTION: glucagon analog ( i i i ) HYPOTHETICAL: No ( i v ) ANTI-SENSE: NO ( x i ) SEQUENCE DESCRIPTION: SEQ ID NO:2:

Ser Gln Gly Thr Phe Thr Ser Gly Tyr Ser Lys Tyr Leu Asp Ser
1 5 10 15

Arg Arg Ala Gln Asp Phe Val Gln Trp Leu Met Asn Thr
20 25

( 2 ) INFORMATION FOR SEQ ID NO:3:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide
( A ) DESCRIPTION: glucagon analog wherein Xaa represents norleucine ( i i i ) HYPOTHETICAL: No ( i v ) ANTI-SENSE: NO ( x i ) SEQUENCE DESCRIPTION: SEQ ID NO:3:

Ser Gln Gly Thr Phe Thr Ser Xaa Tyr Ser Lys Tyr Leu Asp Ser
1 5 10 15

Arg Arg Ala Gln Asp Phe Val Gln Trp Leu Met Asn Thr
20 25

( 2 ) INFORMATION FOR SEQ ID NO:4:

( i ) SEQUENCE CHARACTERISTICS:
( A ) LENGTH: 28 amino acids
( B ) TYPE: amino acid
( C ) STRANDEDNESS: single
( D ) TOPOLOGY: linear -continued (ii) MOLECULE TYPE: peptide
(A) DESCRIPTION: glucagon analog (iii) HYPOTHETICAL: No (iv) ANTI-SENSE: NO (xi) SEQUENCE DESCRIPTION: SEQ ID NO:4:

```
Ser Gln Gly Thr Phe Thr Ser Lys Tyr Ser Lys Tyr Leu Asp Ser
1               5                   10                  15

Arg Arg Ala Gln Asp Phe Val Gln Trp Leu Met Asn Thr
                20                  25
```

(2) INFORMATION FOR SEQ ID NO:5:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide
(A) DESCRIPTION: glucagon analog (iii) HYPOTHETICAL: No (iv) ANTI-SENSE: NO (xi) SEQUENCE DESCRIPTION: SEQ ID NO:5:

```
Ser Gln Gly Thr Phe Thr Ser Glu Tyr Ser Lys Tyr Leu Asp Ser
1               5                   10                  15

Arg Arg Ala Gln Asp Phe Val Gln Trp Leu Met Asn Thr
                20                  25
```

(2) INFORMATION FOR SEQ ID NO:6:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide
(A) DESCRIPTION: glucagon analog (iii) HYPOTHETICAL: No (iv) ANTI-SENSE: NO (xi) SEQUENCE DESCRIPTION: SEQ ID NO:6:

```
Ser Gln Gly Thr Phe Thr Ser Glu Tyr Ser Lys Tyr Leu Asp Ser
1               5                   10                  15

Arg Lys Lys Gln Asp Glu Val Gln Trp Leu Met Asn Thr
                20                  25
```

(2) INFORMATION FOR SEQ ID NO:7:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide
(A) DESCRIPTION: glucagon amide (iii) HYPOTHETICAL: No (iv) ANTI-SENSE: NO -continued ( i x ) FEATURE:
( A ) NAME/KEY: amide group substitution for carboxyl group
( B ) LOCATION: terminus of peptide ( x i ) SEQUENCE DESCRIPTION: SEQ ID NO:7:

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

( 2 ) INFORMATION FOR SEQ ID NO:8:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide
( A ) DESCRIPTION: glucagon analog wherein Xaa represents norleucine ( i i i ) HYPOTHETICAL: No ( i v ) ANTI-SENSE: NO ( i x ) FEATURE:
( A ) NAME/KEY: amide group substitution for carboxyl group
( B ) LOCATION: terminus of peptide ( x i ) SEQUENCE DESCRIPTION: SEQ ID NO:8:

His Ser Gln Gly Thr Phe Thr Ser Xaa Tyr Ala Lys Tyr Leu Asp Gln
1 5 10 15

Arg Arg Ala Gln Asp Phe Val Gln Trp Leu Met Asn Thr
20 25

( 2 ) INFORMATION FOR SEQ ID NO:9:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide
( A ) DESCRIPTION: glucagon analog wherein Xaa represents norleucine ( i i i ) HYPOTHETICAL: No ( i v ) ANTI-SENSE: NO ( i x ) FEATURE:
( A ) NAME/KEY: amide group substitution for carboxyl group
( B ) LOCATION: terminus of peptide ( x i ) SEQUENCE DESCRIPTION: SEQ ID NO:9:

Ser Gln Gly Thr Phe Thr Ser Xaa Tyr Ser Lys Tyr Leu Asp Ala
1 5 10 15

Arg Arg Ala Gln Asp Phe Val Gln Trp Leu Met Asn Thr
20 25

( 2 ) INFORMATION FOR SEQ ID NO:10:

( i ) SEQUENCE CHARACTERISTICS:
( A ) LENGTH: 28 amino acids
( B ) TYPE: amino acid
( C ) STRANDEDNESS: single
( D ) TOPOLOGY: linear -continued ( i i ) MOLECULE TYPE: peptide
( A ) DESCRIPTION: glucagon analog wherein Xaa represents norleucine ( i i i ) HYPOTHETICAL: No ( i v ) ANTI-SENSE: NO ( i x ) FEATURE:
( A ) NAME/KEY: amide group substitution for carboxyl group
( B ) LOCATION: terminus of peptide ( x i ) SEQUENCE DESCRIPTION: SEQ ID NO:10:

| | | | | | | | | | | | | | | |
|---|---|---|---|---|---|---|---|---|---|---|---|---|---|---|
| Ser | Gln | Gly | Thr | Phe | Thr | Ser | Xaa | Tyr | Ala | Lys | Tyr | Leu | Asp | Ala |
| 1 | | | | 5 | | | | | 10 | | | | | 15 |
| Arg | Arg | Ala | Gln | Asp | Phe | Val | Gln | Trp | Leu | Met | Asn | Thr | | |
| | | | | 20 | | | | | 25 | | | | | |

( 2 ) INFORMATION FOR SEQ ID NO:11:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide
( A ) DESCRIPTION: glucagon analog wherein Xaa represents norleucine ( i i i ) HYPOTHETICAL: No ( i v ) ANTI-SENSE: NO ( i x ) FEATURE:
( A ) NAME/KEY: amide group substitution for carboxyl group
( B ) LOCATION: terminus of peptide ( x i ) SEQUENCE DESCRIPTION: SEQ ID NO:11:

| | | | | | | | | | | | | | | |
|---|---|---|---|---|---|---|---|---|---|---|---|---|---|---|
| Ser | Gln | Gly | Thr | Phe | Thr | Ser | Xaa | Tyr | Ala | Lys | Tyr | Leu | Asp | Gln |
| 1 | | | | 5 | | | | | 10 | | | | | 15 |
| Arg | Arg | Ala | Gln | Asp | Phe | Val | Gln | Trp | Leu | Met | Asn | Thr | | |
| | | | | 20 | | | | | 25 | | | | | |

( 2 ) INFORMATION FOR SEQ ID NO:12:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide
( A ) DESCRIPTION: glucagon amide ( i i i ) HYPOTHETICAL: No ( i v ) ANTI-SENSE: NO ( i x ) FEATURE:
( A ) NAME/KEY: amide group substitution for carboxyl group
( B ) LOCATION: terminus of peptide ( x i ) SEQUENCE DESCRIPTION: SEQ ID NO:12:

| | | | | | | | | | | | | | | |
|---|---|---|---|---|---|---|---|---|---|---|---|---|---|---|
| Ser | Gln | Gly | Thr | Phe | Thr | Ser | Glu | Tyr | Ala | Lys | Tyr | Leu | Asp | Ala |
| 1 | | | | 5 | | | | | 10 | | | | | 15 |
| Arg | Arg | Ala | Gln | Glu | Phe | Val | Gln | Trp | Leu | Met | Asn | Thr | | |
| | | | | 20 | | | | | 25 | | | | | |

GLUCAGON ANALOGS WITH SERINE REPLACEMENTS

This invention was made with Government support under U.S. Public Health Grant DK24039. The Government has certain rights in this invention. This application is a continuation Under 1.62 of application Ser. No. 08/175,137 Filed: Dec. 29, 1993, now abandoned.

BACKGROUND OF THE INVENTION

Glucagon is a 29-residue peptide hormone that regulates glycogenesis. The structure of glucagon may be represented as

SEQ ID NO: 1

| | | | | | | | | | | | | | | |
|---|---|---|---|---|---|---|---|---|---|---|---|---|---|---|
| His— | Ser— | Gln— | Gly— | Thr— | Phe— | Thr— | Ser— | Asp— | Tyr— | Ser— | Lys— | Tyr— | Leu— | |
| 1 | 2 | 3 | 4 | 5 | 6 | 7 | 8 | 9 | 10 | 11 | 12 | 13 | 14 | |
| Asp— | Ser— | Arg— | Arg— | Ala— | Gln— | Asp— | Phe— | Val— | Gln— | Trp— | Leu— | Met— | Asn— | Thr |
| 15 | 16 | 17 | 18 | 19 | 20 | 21 | 22 | 23 | 24 | 25 | 26 | 27 | 28 | 29 |

The abbreviations utilized herein are those recommended by IUPAC-IUB [see Eur. J. Biochem. 138, 9 (1984)].

The nomenclature used to define the peptides is that specified by Schroder & Lubke, "The Peptides", Academic Press, (1965), wherein in accordance with conventional representation the amino group at the N-terminal appears to the left and the carboxyl group at the C-terminal to the right. Where the amino acid residue has isomeric forms, it is the L- or naturally occurring form of the amino acid that is represented unless otherwise expressly indicated.

Insulin, as is known, rapidly decreases elevated blood sugar.

It is believed that, in humans, diabetes is only observed when insulin levels are low and glucagon levels are simultaneously elevated. The absence of insulin causes a rapid increase in blood glucose. Large amounts of insulin are required to reduce the glucose levels to normal. The maintenance of stable levels is difficult and subject to considerable fluctuation. This wide fluctuation is responsible, at least in part, for the clinical difficulties experienced in diabetes.

Glucagon appears to act by binding to liver membrane receptors thereby activating adenylate cyclase which, in turn, triggers a series of reactions including the production of cyclic adenosine monophosphate (cAMP), which activates phosphorylase and inhibits glycogen synthetase, thereby contributing to elevated glucose levels in the blood.

Recently considerable effort has been expended to develop glucagon antagonists that will bind to the liver membrane but do not have the ability to transduce the signal to activate adenylate cyclase. One such product is Nα-trinitrophenyl [12-homoarginine]glucagon. This product does bind to the glucagon receptor without significant activation of adenylate cyclase. It also activates another binding system in the hepatocyte membrane leading to the production of inositol trisphosphate and calcium ions. A useful antagonist will block the action of endogenous glucagon by preventing it from binding to the liver membrane receptors and thereby producing cAMP and glucose in the cell, and the ultimate elevation of blood sugar. Such products would be useful to reduce a diabetic's need for injections or infusion of insulin.

An ideal glucagon antagonist would (1) be completely inactive toward stimulation of adenylate cyclase and production of cAMP, (2) bind as well as glucagon itself to the liver membrane receptor, (3) compete with glucagon for receptor binding, (4) at moderate concentrations fully inhibit the action of glucagon toward the activation of adenylate cyclase, and (5) have a satisfactory inhibition index.

The inhibition index is the molar ratio of antagonist to agonist which reduces the biological response 50% of the value in the absence of antagonist. It will be discussed more fully hereinafter.

U.S. Pat. Nos. 4,879,273 and 5,143,902 describe certain useful glucagon analogs in which the aspartic acid residue at the 9-position of the glucagon molecule is removed or replaced with another amino acid residue either in the D-form or the L-form. The replacement may be selected from any of a number of amino acids both natural and synthetic, including hydrophobic and hydrophilic amino acids, aliphatic amino acids, aryl amino acids, basic amino acids and acidic amino acids.

It was observed that compounds of the class described in these patents either with or without the histidine residue at the 1-position are useful adjuncts to insulin therapy in the control of blood glucose levels. The preferred compounds for such utility, as disclosed in the prior patents are:

des $His^1[Gly^9]$glucagon SEQ ID NO:2
des $His^1[Nle^9]$glucagon SEQ ID NO:3
des $His^1[Lys^9]$glucagon SEQ ID NO:4
des $His^1[Glu^9]$glucagon SEQ ID NO:5
des $His^1[Glu^9Lys^{17,18}\ Glu^{21}]$glucagon SEQ ID NO:6 and the corresponding carboxy terminal amides of such compounds.

It has now been discovered that the utility of the compounds of the previous patents for the treatment of diabetes can be remarkably and surprisingly improved by replacement of the serine residue at the 16-position and the optional replacement of the serine residue at the 11-position and/or the aspartic acid residue at the 21-position. However, the key to the utility of the compounds is still the 9-position.

THE INVENTION

A novel class of glucagon antagonists has now been discovered which substantially fulfills the criteria listed above with surprising improvements and minimum side effects. The class is characterized by the deletion or replacement of the aspartic acid residue at the 9-position coupled with replacement of the serine residue at the 16-position and the optional replacement of amino acid residues at other positions. It has been observed that, generally, deletion of the histidine residue at the 1-position improves the desirable characteristics of the products of this invention.

More specifically, the products of this invention, in addition to the position modifications outlined above are characterized by a binding activity of at least about 40% relative to glucagon, an inhibition index up to about 10 and an adenylate cyclase activity up to about 1% glucaton. These remarkably improved therapeutic parameters have been made possible by the discovery by the discovery of the significant contribution to binding and transduction made possible by modifications in the glucagon molecule at positions other than the 1- and the 9-positions, especially by modifications of the 16-position.

The replacement amino acid residues at the 16-position or, if desired, at the 11- and 21-positions are natural and synthetic aliphatic amino acids, preferably those containing up to five carbon atoms.

The products of this invention were synthesized by known solid phase techniques. See, for example, Barany and Merrifield (1979) in The Peptides, eds. Gross and Meienhofer (Academic Press, New York) vol. 2A, pages 1 to 284. The products can be prepared by manual methods or, for example, on a peptide synthesizer such as the Applied Biosystems 430 unit.

Analogs with a free C-terminal carboxyl were made on phenylacetamidomethyl-resin supports, and those with C-terminal amides were made on a methylbenzhydrylamine-resin. Side chain protection was Arg(Tos), Asp(OcHx), Glu(OcHx), His(Tos), Lys(ClZ), Ser(Bzl), Thr(Bzl), Trp-(For), and Tyr(BrZ). Double couplings with preformed symmetric anhydrides in dimethylformamide were used routinely for all tert-butyloxycarbonyl-protected amino acids except for tosyl arginine, glutamine, and asparagine, where N-hydroxybenzotriazole esters in dimethylformamide were required [Konig, W. & Gieger, R. Chem. Ber. 103, 788 (1970)]. The assembled protected peptide-resins were cleaved by the "low/high HF" technique [Tam, J. P., Heath, W. F. & Merrifield, R. B. J. Am. Chem. Soc. 105, 6442 (1983)], which was developed to avoid a number of potential side reactions. After evaporation of HF and washing with ether,the crude free peptide was extracted with 10% acetic acid and lyophilized. Purification of the synthetic peptides was performed by preparative low-pressure reverse-phase liquid chromatography on $C_{18}$-silica as described [Andreu, D. & Merrifield, R. B. in Peptides: Structure and Function, eds. Deber, C. M., Hruby, V. J. & Kopple, K. D. (Pierce Chem. Co., Rockford, Ill.), pp. 595–598. The overall yields were between 35 and 40%. Homogeneity was demonstrated by analytical HPLC, and identity was confirmed by amino acid analysis, mass spectroscopy and molecular weight determinations.

The amino acid analysis of all compounds prepared agreed with theory within ±5%, and the molecular weights determined by mass spectrometry were within 0.5 mass units.

Tert-Butyloxycarbonyl (Boc) protected amino acids were from Peninsula Laboratories, (San Carlos, (A.) p-methylbenzhydrylamine resin (0.45 mmol/g) was from United States Biochemical (Cleveland, Ohio) and boc-Thr-(Bzl)-4-oxymethylphenylacetamidomethyl copoly (styrene-1°% divinyl benzene) was prepared as described by Mitchell et al, J. Org. Chem. 43, 2845 (1978).

$^{125}$I-labeled glucagon from New England Nuclear was used without further purification for periods up to 1 month after its preparation. Creatine phosphate, creatine kinase, bovine serum albumin, dithiothreitol, GTP, and ATP were from Sigma. A cAMP assay kit containing [8-$^{3}$H]cAMP was from Amersham. Nuflow membrane filters (0.45 um) were from Oxoid (Basingstoke, England).

Various tests were employed to determine the efficacy of the products of this invention. These included the membrane receptor binding assay and adenyl cyclase assays.

Membrane Binding Assay. Liver plasma membranes were prepared from male Sprague-Dawley rats (Charles River Breeding Laboratories) by the Neville procedure as described by Pohl [Pohl, S. L. (1976) in Methods in Receptor Research, ed. Blecher, M. (Marcel Dekker, New York), pp. 160–164]. The receptor binding assay was as described by Wright and Rodbell [Wright, D. E. & Rodbell, M. (1979) J. Biol. Chem. 254, 268–269] in which competition for glucagon receptors between $^{125}$I-labeled natural glucagon (1.6 nM) and the unlabeled synthetic analog was measured. After correction for the blank, the percentage of displacement of label was compared with that of a purified glucagon standard, and the relative binding affinity was calculated.

Adenylate Cyclase Assay. The assay on liver membranes was performed according to Salomon et al. [Salomon, Y., Londos, C. & rodgell, M. Anal. Biochem. 58, 541, 548 (1974)]. The released cAMP was mixed with [8-$^{3}$H]cAMP measured with a high affinity cAMP binding protein.

The purpose of the membrane binding assay is to measure the ability of analogs of glucagon to bind to liver membrane receptor compared to that of glucagon.

When the glucagon analogs of this invention were assayed, they were assayed as amides with natural glucagon amide as a standard, thus eliminating the possibility of imprecision due to the heterogeneity of membrane preparations. In fact, it presently appears that C-terminal amides are more active than the corresponding carboxyl compounds. Accordingly, C-terminal amides of the glucagon analogs of the invention are the presently preferred compounds of the invention.

The relative binding affinity of a given analog is expressed as:

$$\frac{\text{(half maximal displacement concentration of glucagon)}}{\text{(half maximal displacement concentration of analog)}} \times 100$$

The purpose of the adenylate cyclase assay is to measure the ability of the compound under test to stimulate the activity of adenylate cyclase. The assays are used to measure relative potency, maximum activity and inhibition index.

The inhibition index, defined above, was determined from adenylate cyclase assays by two different protocols.

1. A glucagon standard curve for cAMP vs glucagon concentration was established. Then another glucagon assay curve was measured in the presence of a constant amount of antagonist. The concentration of glucagon that had its activity reduced to 50% by that concentration of inhibitor was then determined.
2. A series of tubes were set up containing an amount of glucagon which will produce 90% of maximum response. Increasing amounts of antagonist were then added and the concentration that reduced the response to 45% of maximum was determined.

The compounds of this invention have an inhibition index less than 10, membrane receptor binding activity of at least 40% compared to glucagon and an adenylate cyclase activity up to about 1% of glucagon.

In the most preferred compounds of this invention the $pA_2$ value is at least 5 and preferably above 7.

The $pA_2$ value is the negative logarithm of the concentration of antagonist that reduces the response to 1 unit of agonist to the response obtained from 0.5 unit of agonist.

The following table shows the results of measurements with glucagon and certain of the presently preferred compounds of this invention measured as amides.

TABLE 1

| Analog of glucagon amide | % Binding Activity | % Relative Activity | $(I/A)_{50}$ | $pA_2$ | |
|---|---|---|---|---|---|
| Glucagon amide | 100 | 15 | | | SEQ ID NO: 7 |
| 1. $Nle^9Ala^{11}Gln^{16}$ | 46.8 | 0.003 | 1.6 | 8.7 | SEQ ID NO: 8 |
| 2. des-$His^1Nle^9Ala^{16}$ | 100 | 0.001 | 2.14 | 8.4 | SEQ ID NO: 9 |
| 3. des-$His^1Nle^9Ala^{11}Ala^{16}$ | 100 | 0.0043 | 0.85 | 8.4 | SEQ ID NO: 10 |
| 4. des-$His^1Nle^9Ala^{11}Gln^{16}$ | 56.3 | 0.0011 | 2.2 | 8.4 | SEQ ID NO: 11 |
| 5. des-$His^1Glu^9Ala^{11}Ala^{16}Glu^{21}$ | 39 | 0.016 | 2.57 | 8.5 | SEQ ID NO: 12 |

The glucagon analogs of this invention also include derivatives having the defined properties. As indicated above, C-terminal amides are actually preferred over the C-terminal carboxyl compounds. Side chain amides such as amides of dibasic acids are also useful. Esters, especially those based on alkyl or aralkyl alcohols corresponding to the amides may also be employed. Ethers, especially lower alkyl ethers of analogs including Ser, Thr and Tyr amino acid residues are also useful, as are esters of these analogs based on alkyl, aryl and aralkyl acids. Glucagon analogs containing amino acid residues with additional functional group may also be converted to derivatives within the scope of the invention. These might include, for example N-acetyl derivatives of diamino acids such as lysine.

One class of useful derivatives is based on des-$His^1$ glucagon analogs in which the amino group of the amino terminal serine residue has been converted to a 2,4-difluorobenzoyl amide. Other hydroxyl and amine substituted amino acids derivatized with 2,4-difluorobenzoic acid are within the scope of the invention whether or not the histadyl residue at the 1-position is in place.

In some instances, compounds within the scope of the invention may be synthesized and thereafter utilized with one or more of the blocking groups still in place.

The products of this invention will generally be administered in the same manner as insulin, i.e. parenterally or by infusion. Since their chemical structure and activity is quite similar to insulin, they will generally be administered with the same types of pharmaceutically acceptable excipients as insulin. They may in fact be coadministered with insulin in the same dosage units. They may also be administered simultaneously with the insulin although not in the same composition.

Since the products of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrogromic acids. Such products are readily prepared by procedures well known to those skilled in the art.

The products of the invention will normally be provided for as parenteral compositions for injection or infusion. They can, for example be suspended in an inert oil, suitably a vegetable oil such as sesame, peanut, or olive oil, alternatively they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly when the buffer contains sodium ions.

If desired the solutions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkaryl polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of glucagon analog which will be effective in one or multiple doses to control glucoenesis and ketogenesis at the selected level, normally in the presence of insulin. As will be recognized by those skilled in the art, an effective amount of the therapeutic agent will vary with many factors including the age and weight of the patient, the amount of insulin which is concurrently employed, the blood sugar level to be obtained, the inhibition index of the selected analog, and other factors. Typical dosage units will contain from 0.2 to 0.8 ug/ml although wide variations from this range are possible while yet achieving useful results.

What is claimed is:

1. A peptide consisting of a glucagon analog wherein (a) Histidine at the 1-position is either present or absent, (b) the aspartic acid residue at the 9-position is either absent or replaced with another amino acid residue, (c) the serine residue at the 11-position is optionally replaced with an aliphatic amino acid residue, (d) the serine residue at the 16-position is replaced with an aliphatic amino acid residue, (e) the aspartic acid residue at the 21-position is optionally replaced with an aliphatic amino acid residue, and (f) the carboxy terminus is optionally amidated, said analog being further characterized by a relative membrane receptor binding activity compared to glucagon of at least about 40%, an inhibition index up to about 10 and an adenylate cyclase activity up to about 1% of that of glucagon and pharmaceutically acceptable acid addition salts of said analogs.

2. The glucagon analog of claim 1 wherein the serine residue at the 11-position, the aspartic acid residue at the 21-position or both the serine residue and the aspartic acid residue are replaced with an aliphatic amino acid.

3. The glucagon analog of claim 1 wherein the histidine at the 1-position is absent or a pharmaceutically acceptable acid addition salt thereof.

4. The glucagon analog of claim 2 wherein the histidine at the 1-position is absent or a pharmaceutically acceptable acid addition salt thereof.

5. The glucagon analog of claim 1 wherein said carboxy terminus is amidated.

6. The glucagon analog of claim 2 wherein said carboxy terminus is amidated.

7. $Nle^9Ala^{11}Gln^{16}$ glucagon amide SEQ ID NO:8.

8. des-$His^1Nle^9Ala^{16}$ glucagon amide SEQ ID NO:9.

9. des-$His^1Nle^9Ala^{11}Ala^{16}$ glucagon amide SEQ ID NO:10.

10. des-$His^1Nle^9Ala^{11}Gln^{16}$ glucagon amide SEQ ID NO:11.

11. des-$His^1Glu^9Ala^{11}Ala^{16}Glu^{21}$ glucagon amide SEQ ID NO:12.

12. A parenteral composition for the control of glucogenesis and ketoacidosis in humans containing a pharmaceutically acceptable carrier and an amount of a glucagon analog which is effective to achieve such control, said analog consisting of a peptide wherein (a) Histidine at the 1-position is either present or absent, (b) the aspartic acid residue at the 9-position is either absent or replaced with another amino acid residue, (c) the serine residue at the 16-position is replaced with an aliphatic amino acid residue, (d) the serine residue at the 11-position is optionally replaced with an aliphatic amino acid residue, (e) the aspartic acid residue at the 21-position is optionally replaced with an aliphatic amino acid residue, and (f) the carboxy terminus is optionally amidated said analog being further characterized by a relative membrane receptor binding activity compared to glucagon of at least about 40%, an inhibition index up to about 10 and an adenylate cyclase activity up to about 1% of that of glucagon and pharmaceutically acceptable acid addition salts of said analogs.

13. The parenteral composition of claim 12 wherein in the glucagon analogue the serine residue at the 11-position, the aspartic acid residue at the 21-position or both the serine residue and the aspartic acid residue are replaced with an aliphatic amino acid.

14. The parenteral composition of claim 12 wherein the histidine at the 1-position of the glucagon analog is absent.

15. The parenteral composition of claim 13 wherein the histidine at the 1-position of the glucagon analog is absent.

16. The parenteral composition of claim 12 wherein the carboxy terminus is amidated.

17. The parenteral composition of claim 16 wherein the serine residue at the 11-position, the aspartic acid residue at the 21-position or both the serine residue and the aspartic acid residue are replaced with an aliphatic amino acid.

18. The parenteral composition of claim 14 wherein the carboxy terminus is amidated.

19. The parenteral composition of claim 18 wherein in the glucagon analogue the serine residue at the 11-position, the aspartic acid residue at the 21-position or both the serine residue and the aspartic acid residue are replaced with an aliphatic amino acid.

20. A parenteral composition of claim 12 wherein the glucagon analog is $Nle^9Ala^{11}Gln^{16}$ glucagon amide SEQ ID NO:8.

21. A parenteral composition of claim 12 wherein the glucagon analog is des-$His^1Nle^9Ala^{16}$ glucagon amide SEQ ID NO:9.

22. A parenteral composition of claim 12 wherein the glucagon analog is des-$His^1Nle^9Ala^{11}Ala^{16}$ glucagon amide SEQ ID NO:10.

23. A parenteral composition of claim 12 wherein the glucagon analog is des-$His^1Nle^9Ala^{11}Gln^{16}$ glucagon amide SEQ ID NO:11.

24. A parenteral composition of claim 12 wherein the glucagon analog is des-$His^1Glu^9Ala^{11}Ala^{16}Glu^{21}$ glucagon amide SEQ ID NO:12.

25. A parenteral composition in dosage unit form for the control of glucogenesis and ketoacidosis in humans containing a pharmaceutically acceptable carrier and from about 0.2 to 0.8 ug/ml of a glucagon analog consisting of a peptide wherein (a) Histidine at the 1-position is either present or absent, (b) the aspartic acid residue at the 9-position is either absent or replaced with another amino acid residue, (c) the serine residue at the 16-position is replaced with an aliphatic amino acid residue, (d) the serine residue at the 11-position is optionally replaced with an aliphatic amino acid residue, (e) the aspartic acid residue at the 21-position is optionally replaced with an aliphatic amino acid residue, and (f) the carboxy terminus is optionally amidated said analog being further characterized by a relative membrane receptor binding activity compared to glucagon of at least about 40%, an inhibition index up to about 10 and an adenylate cyclase activity up to about 1% of that of glucagon and pharmaceutically acceptable acid addition salts of said analogs.

26. The parenteral composition of claim 25 wherein in the glucagon analogue the serine residue at the 11-position, the aspartic acid residue at the 21-position or both the serine residue and the aspartic acid residue are replaced with an aliphatic amino acid.

27. The parenteral composition of claim 25 wherein the histidine at the 1-position of the glucagon analog is absent.

28. The parenteral composition of claim 27 wherein in the glucagon analogue the serine residue at the 11-position, the aspartic acid residue at the 21-position or both the serine residue and the aspartic acid residue are replaced with an aliphatic amino acid.

29. The parenteral composition of claim 25 wherein the carboxy terminus is amidated.

30. The parenteral composition of claim 29 wherein in the glucagon analogue the serine residue at the 11-position, the aspartic acid residue at the 21-position or both the serine residue and the aspartic acid residue are replaced with an aliphatic amino acid.

31. The parenteral composition of claim 27 wherein the carboxy terminus is amidated.

32. The parenteral composition of claim 30 wherein in the glucagon analogue the serine residue at the 11-position, the aspartic acid residue at the 21-position or both the serine residue and the aspartic acid residue are replaced with an aliphatic amino acid.

33. The parenteral composition of claim 25 wherein the glucagon analog is $Nle^9Ala^{11}Gln^{16}$ glucagon amide [SEQ. ID No: 8].

34. The parenteral composition of claim 25 wherein the glucagon analog is des-$His^1Nle^9Ala^{16}$ glucagon amide [SEQ. ID No: 9].

35. The parenteral composition of claim 25 wherein the glucagon analog is des-$His^1Nle^9Ala^{11}Ala^{16}$ glucagon amide [SEQ. ID No: 10].

36. The parenteral composition of claim 25 wherein the glucagon analog is des-$His^1Nle^9Ala^{11}Gln^{16}$ glucagon amide [SEQ. ID No: 11].

37. The parenteral composition of claim 25 wherein the glucagon analog is des-$His^1Glu^9Ala^{16}Glu^{21}$ glucagon amide [SEQ. ID No: 12].

* * * * *